US012740945B2

(12) United States Patent
Zhang et al.

(10) Patent No.: US 12,740,945 B2
(45) Date of Patent: Sep. 22, 2026

(54) circCDK13-ENRICHED ENGINEERED SMALL EXTRACELLULAR VESICLE (E-sEV), AND PREPARATION METHOD AND USE THEREOF

(71) Applicant: CHINESE PLA GENERAL HOSPITAL, Beijing (CN)

(72) Inventors: Cuiping Zhang, Beijing (CN); Qilin Huang, Beijing (CN); Kui Ma, Beijing (CN); Ziqiang Chu, Beijing (CN); Xiaobing Fu, Beijing (CN)

(73) Assignee: CHINESE PLA GENERAL HOSPITAL, Beijing (CN)

(*) Notice: Subject to any disclaimer, the term of this patent is extended or adjusted under 35 U.S.C. 154(b) by 189 days.

(21) Appl. No.: 18/613,014

(22) Filed: Mar. 21, 2024

(65) Prior Publication Data

US 2025/0000807 A1 Jan. 2, 2025

(30) Foreign Application Priority Data

Jun. 29, 2023 (CN) ......................... 202310785819.2

(51) Int. Cl.

| | |
|---|---|
| ***A61K 9/50*** | (2006.01) |
| ***A61K 31/7105*** | (2006.01) |
| ***A61P 17/02*** | (2006.01) |
| ***B01D 21/26*** | (2006.01) |
| ***B01D 61/14*** | (2006.01) |
| ***B01D 69/02*** | (2006.01) |
| ***C12N 5/0775*** | (2010.01) |
| ***C12N 15/86*** | (2006.01) |

(52) U.S. Cl.

CPC ........ *A61K 9/5068* (2013.01); *A61K 31/7105* (2013.01); *A61P 17/02* (2018.01); *B01D 21/262* (2013.01); *B01D 61/147* (2013.01); *B01D 69/02* (2013.01); *C12N 5/0662* (2013.01); *C12N 15/86* (2013.01); *B01D 2311/02* (2013.01); *B01D 2325/0283* (2022.08); *C12N 2510/02* (2013.01); *C12N 2740/15043* (2013.01)

(58) Field of Classification Search

None

See application file for complete search history.

(56) References Cited

PUBLICATIONS

Ma et al., Cell Biol. Toxicol. (2023), 39, pp. 497-518.*

Gao et al., Frontiers in Bioengineering and Biotechnology (2023), 10, DOI 10.3389/fbioe.2022.1100892 (17pages).*

* cited by examiner

*Primary Examiner* — Brian J Davis

(74) *Attorney, Agent, or Firm* — NGUYEN TARBET IP LAW

(57) ABSTRACT

The present disclosure provides a circCDK13-enriched engineered small extracellular vesicle (E-sEV), and a preparation method and use thereof, and belongs to the technical field of biomedicine. The present disclosure provides a preparation method of the circCDK13-enriched E-sEV. In the present disclosure, human placenta-derived mesenchymal stem cells (hP-MSCs) are infected with a vector overexpressing circCDK13, and a resulting cell supernatant is collected to obtain a small extracellular vesicle (sEV) overexpressing the circCDK13, which is used for wound healing in diabetes mellitus (DM). The E-sEV shows a therapeutic effect on DM wounds that is significantly better than that of natural small extracellular vesicles (N-sEVs) secreted by the hP-MSCs. This product not only exhibits advantages in healing speed, but also has a greater application potential in stimulating skin appendage regeneration and improving the quality of wound healing.

13 Claims, 12 Drawing Sheets

Specification includes a Sequence Listing.

N-sEVs circcDK13$^{OE}$-sEVs circCDK13-ENRICHED ENGINEERED SMALL EXTRACELLULAR VESICLE (E-sEV), AND PREPARATION METHOD AND USE THEREOF

CROSS REFERENCE TO RELATED APPLICATION

This patent application claims the benefit and priority of Chinese Patent Application No. 2023107858192, filed with the China National Intellectual Property Administration on Jun. 29, 2023, the disclosure of which is incorporated by reference herein in its entirety as part of the present application.

REFERENCE TO AN ELECTRONIC SEQUENCE LISTING

The contents of the electronic sequence listing (name of the file: Sequence listing-Original.xml; Size: 4,438 bytes; and Date of Creation: 2023 Jun. 16) is herein incorporated by reference in its entirety.

TECHNICAL FIELD

The present disclosure belongs to the technical field of biomedicine, and specifically relates to a circCDK13-enriched engineered small extracellular vesicle (E-sEV), and a preparation method and use thereof.

BACKGROUND

Circular RNAs (circRNAs) are a special type of non-coding RNA that do not have a 5'-end cap and a 3'-end poly (A) tail. The 3'- and 5'-ends are ligated through exon cyclization or intron cyclization to form a complete circular structure, thus avoiding degradation by exonucleases. Therefore, the circRNAs have a longer half-life and greater conservation than those of linear RNAs. Accordingly, the circRNAs show unique advantages in disease diagnosis and development of treatment strategies.

Delayed healing or non-healing of wounds is an important complication that leads to severe disability and death in patients with diabetes mellitus (DM), and seriously affects the life quality of patients, bringing a huge economic burden to families and society. In recent years, researchers have gradually realized that circRNAs are also important players in the skin wound repair process with in-depth research on the circRNAs. Previous studies have confirmed that circCDK13 (circBase ID: hsa_circ_0079929) can improve the function of fibroblasts and keratinocytes in skin tissue, thereby promoting wound healing in the DM. However, the circCDK13 consists of 660 bases and is difficult to be directly synthesized in vitro like microRNAs. In addition, due to its large molecular diameter, circCDK13 is difficult to penetrate the cell membrane and be absorbed by cells in direct applications. As a result, it is particularly important to explore a safe, feasible, and efficient circRNA delivery strategy.

Small extracellular vesicles (sEVs) are nanoscale particles wrapped by a lipid bilayer membrane, with a diameter of 50 nm to 200 nm, and contain a variety of non-coding RNAs (such as microRNA, IncRNA, and circRNA), mRNA, and DNA as well as proteins, and lipids and other substances. The sEVs can transfer proteins and nucleic acids to nearby or distant cells and are therefore considered important messengers for intercellular communication. Compared with cell therapy, sEVs as a cell-free therapy strategy have better stability, lower immunogenicity, fewer ethical issues, and fewer risks of embolism and tumor occurrence. In addition, sEVs are easily taken up by cells and show desirable protective capabilities for the bioactive components they encapsulate. In view of this, the sEVs are favored by researchers in the fields of immunotherapy, regenerative medicine, and drug delivery.

SUMMARY

A purpose of the present disclosure is to provide a circCDK13-enriched E-sEV, and a preparation method and use thereof. In the present disclosure, the E-sEV has a stronger biological activity than that of natural small extracellular vesicles (N-sEVs) and can accelerate wound healing and the regeneration of appendages.

The present disclosure provides a preparation method of a circCDK13-enriched E-sEV, including the following steps: infecting a mesenchymal stem cell (MSC) with a vector overexpressing circCDK13, and extracting a small extracellular vesicle (sEV) from a resulting infected positive MSC to obtain the circCDK13-enriched E-sEV.

Preferably, the vector overexpressing the circCDK13 includes a lentivirus overexpressing the circCDK13.

Preferably, the preparation method further includes culturing the infected positive MSC, collecting a resulting cell supernatant, and extracting the circCDK13-enriched E-sEV from the cell supernatant.

Preferably, the infected positive MSC is cultured in an MSC-specific serum-free medium.

Preferably, a process of the extracting includes differential centrifugation.

Preferably, the differential centrifugation includes: subjecting the infected positive MSC to first centrifugation, subjecting an obtained first centrifugation supernatant to second centrifugation, subjecting an obtained second centrifugation supernatant to third centrifugation, and collecting an obtained precipitate;

the first centrifugation is conducted at 3,000 g to 4,000 g, the second centrifugation is conducted at 10,000 g to 12,000 g, and the third centrifugation is conducted at 100,000 g to 200,000 g.

Preferably, the first centrifugation is conducted for 15 min; the second centrifugation is conducted for 60 min; and the third centrifugation is conducted for 90 min.

Preferably, the second centrifugation supernatant is filtered with a filter membrane having a pore size of 0.22 μm before the third centrifugation is conducted.

The present disclosure further provides a circCDK13-enriched E-sEV prepared by the preparation method.

The present disclosure further provides use of the circCDK13-enriched E-sEV in preparation of a drug for promoting wound healing in DM.

Beneficial effects: the present disclosure provides a preparation method of a circCDK13-enriched E-sEVs, where an MSC is infected with a circCDK13-carrying vector, and a resulting cell supernatant is collected to obtain a circCDK13-overexpressing sEV. The E-sEV has a stronger biological activity than that of N-sEVs. In the present disclosure, the circCDK13-enriched E-sEV is used for DM wounds. The E-sEV shows a therapeutic effect on DM wounds that is significantly better than that of natural small extracellular vesicles (N-sEVs) secreted by the hP-MSCs. This product not only exhibits advantages in healing speed, but also has a greater application potential in stimulating skin appendage regeneration and improving the quality of wound healing.

DETAILED DESCRIPTION OF THE EMBODIMENTS

Figure 1A:
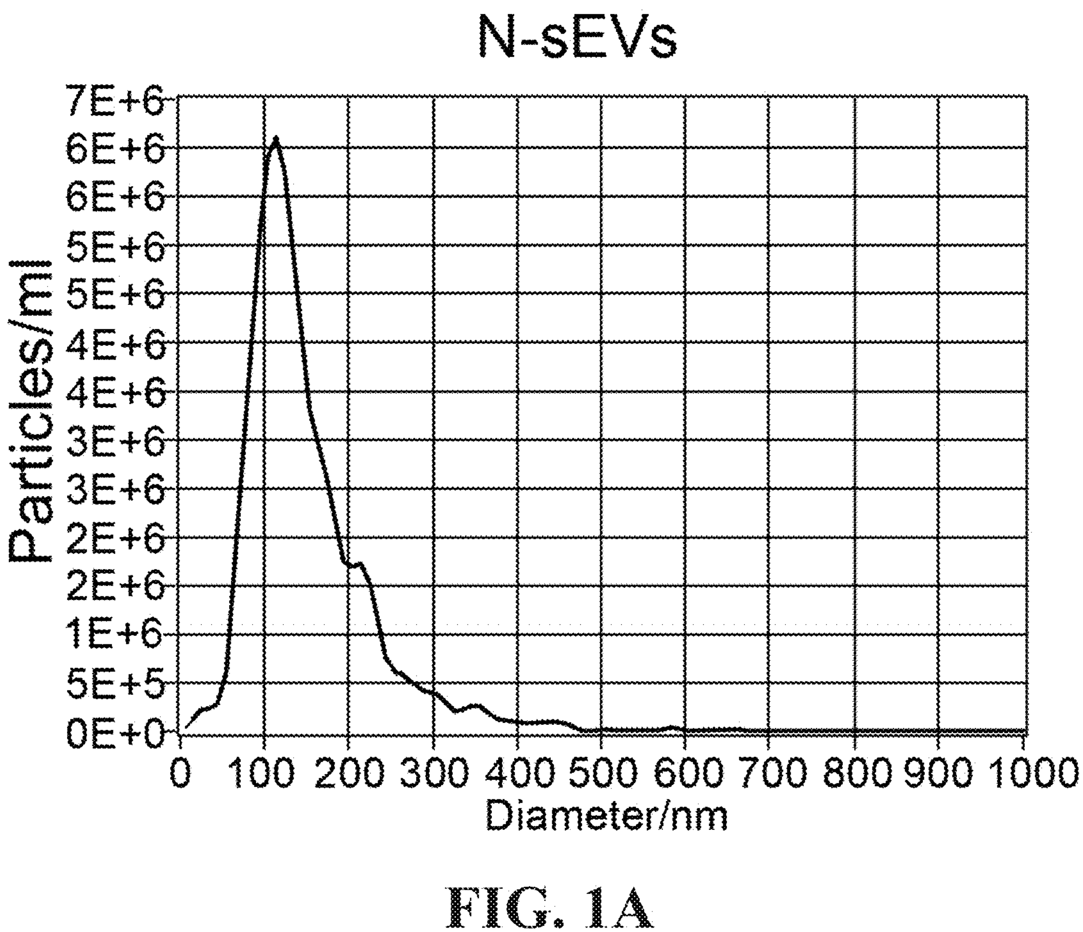
FIGS. 1A-1B show the detection results of a particle size and a particle concentration of a human placenta-derived mesenchymal stem cell-based engineered small extracellular vesicle (hP-MSC E-sEV) in Example 1 of the present disclosure.

The present disclosure provides a preparation method of a circCDK13-enriched E-sEV, including the following steps: infecting a mesenchymal stem cell (MSC) with a vector overexpressing circCDK13, and extracting a small extracellular vesicle (sEV) from a resulting infected positive MSC to obtain the circCDK13-enriched E-SEV.

In the present disclosure, the so-called vector (Vector) refers to a self-replicating DNA molecule that transfers DNA fragments (target genes) to recipient cells in genetic engineering recombinant DNA technology, including common bacterial plasmids, phages, and animal and plant viruses. The Vector in the examples refers to a lentivirus. The vector overexpressing the circCDK13 preferably includes a lentivirus overexpressing the circCDK13. There are no special restrictions on a construction method of the lentivirus. The lentivirus can be entrusted to a company to construct, and only needs to meet the requirements for overexpressing circCDK13 (circBase ID: hsa-_circ_0079929).

In the present disclosure, the vector overexpressing circCDK13 is used to infect the MSC, and the hP-MSC preferably has a cell confluence of 40% to 50%. There is no particular limitation on a process of the infecting. In an example, an infection-enhancing solution is added to allow infection, and puromycin is added 48 h after the infection to obtain infected positive MSCs stably expressing the circCDK3. The MSCs preferably include hP-MSCs (also called chorionic plate-derived mesenchymal stem cells, CP-MSCs), human umbilical cord-derived mesenchymal stem cells (hUC-MSCs), human adipose-derived mesenchymal stem cells (hA-MSCs), and bone marrow-derived mesenchymal stem cells (B-MSCs).

In the present disclosure, the preparation method further includes preferably culturing the infected positive MSC, collecting a resulting cell supernatant, and extracting the circCDK13-enriched E-sEV from the cell supernatant. The infected positive MSC is preferably cultured in an MSC-specific serum-free medium. Preferably, differential centrifugation is conducted to extract a large number of cultured infected positive MSCs; the extraction preferably includes differential centrifugation, and more preferably includes: subjecting the infected positive MSC to first centrifugation, subjecting an obtained first centrifugation supernatant to second centrifugation, subjecting an obtained second centrifugation supernatant to third centrifugation, and collecting an obtained precipitate;

the first centrifugation is conducted at 3,000 g to 4,000 g, the second centrifugation is conducted at 10,000 g to 12,000 g, and the third centrifugation is conducted at 100,000 g to 200,000 g.

In the present disclosure, the first centrifugation is conducted for preferably 15 min; the second centrifugation is conducted for preferably 60 min; and the third centrifugation is conducted for preferably 90 min. The second centrifugation supernatant is preferably filtered with a filter membrane having a pore size of preferably 0.22 μm before the third centrifugation is conducted. After the precipitate is obtained by the third centrifugation, the precipitate is preferably resuspended in PBS (with a pH value of 7.2 to 7.4) to allow the third centrifugation again, and resuspended again to obtain the circCDK13-enriched E-sEV.

The present disclosure further provides a circCDK13-enriched E-sEV prepared by the preparation method.

In the present disclosure, the circCDK13-enriched E-sEV has a typical cup-shaped structure with an average diameter of approximately 114 nm, and can overexpress circCDK13, while the overexpression of circCDK13 does not affect the appearance and diameter of sEVs. Western blot is conducted to detect characteristic membrane proteins, showing positive for CD63, CD9, and TSG101.

The present disclosure further provides use of the circCDK13-enriched E-sEV in preparation of a drug for promoting wound healing in DM.

In the examples of the present disclosure, controlled experiments in a DM mouse model have confirmed that N-sEVs secreted from CP-MSCs can promote wound healing in DM mice. The ability of circCDK13-loaded sEVs in promoting the wound healing is significantly enhanced, and circCDK13-sEVs can accelerate wound healing and the regeneration of appendages, making wound repair more perfect.

In order to further illustrate the present disclosure, the circCDK13-enriched E-sEV, and the preparation method and the use thereof provided by the present disclosure are described in detail below with reference to the accompanying drawings and examples, but the accompanying drawings and the examples should not be construed as limiting the protection scope of the present disclosure.

Example 1

1. Preparation of circCDK13-enriched E-sEV, CircCDK13$^{OE}$-SEVs (1) CircCDK13 lentivirus and lentivirus Vector were constructed by Guangzhou Geneseed Biotech Co., Ltd.

(2) CP-MSCs were inoculated into a T25 culture bottle and cultured in a constant-temperature incubator at 37° C. with CO2 at a volume fraction of 5%.

(3) When the cell confluence reached 40% to 50%, the circCDK13 lentivirus or Vector was added to the cultured cells and added with a corresponding infection-enhancing solution.

(4) 48 h after infection, puromycin (2 μg/mL) was added to the cell medium to obtain CP-MSCs stably expressing circCDK3.

(5) Large-scale culture of circCDK13 overexpressing CP-MSCs (circCDK13-OE group) and its control CP-MSCs (Control group) was conducted in an MSC serum-free medium.

(6) When the cell confluence reached 80% to 90%, a resulting cell supernatant was collected for isolation of sEVs, while CP-MSCs continued to be subcultured.

(7) The cell supernatant was centrifuged in a centrifuge tube at 4° C. and 300 g for 10 min.

(8) A resulting supernatant was collected while discarding the precipitate, and the supernatant was centrifuged at 3,000 g and 4° C. for 15 min.

(9) A resulting supernatant was collected while discarding the precipitate, and the supernatant was centrifuged at 10,000 g and 4° C. for 60 min.

(10) A resulting supernatant was collected while discarding the precipitate, and the supernatant was filtered through a 0.22 μm filter.

(11) A collected filtrate was centrifuged in an ultra-high-speed centrifuge at 200,000 g and 4° C. for 90 min.

(12) A resulting supernatant was discarded, and a resulting precipitate was resuspended in sterile PBS, and centrifuged at 4° C. and 200,000 g for 90 min.

(13) A resulting supernatant was discarded, and a resulting precipitate was resuspended in sterile PBS to obtain a sEVs suspension. The collected sEVs were divided and stored at −80° C., and the isolated sEVs were subsequently identified.

2. Western blot detection of sEVs surface marker proteins (1) The concentration of sEVs protein was measured with a BCA protein quantification kit.

(2) Based on the protein quantification results, a loading amount of sEVs was calculated (10 μg to 30 μg), a 5× protein loading buffer was added in proportion, mixed well by vortex, and heated in a 100° C. metal bath for 10 min, and obtained denatured proteins were subjected to SDS-PAGE electrophoresis.

(3) The positive protein markers CD9, TSG101, and CD63 and the negative protein marker Calnexin of exosomes, namely "three positives and one negative", were detected. The dilution ratios of primary antibodies were as follows: CD63 (1:1000), CD9 (1:1000), TSG101 (1:2000), Calnexin (1:5000).

3. Electron microscopy detection of sEVs (1) 10 μL of sEVs solution was added dropwise onto a copper grid, incubated at room temperature for 10 min, rinsed with sterile distilled water, and excess liquid was removed by absorbent paper.

(2) 10 μL of 2% uranyl acetate was added dropwise to the copper grid to allow negative staining for 1 min, the floating liquid was removed with filter paper, and the copper grid was dried under an incandescent lamp for 2 min.

(3) The copper grid was observed under TEM and imaged at 80 kV.

4. Nanoparticle tracking analysis (NTA) detection of sEVs (1) A sample cell was washed with deionized water.

(2) The instrument was calibrated with polystyrene microspheres (100 nm).

(3) The sample cell was washed with 1×PBS buffer.

(4) An appropriate amount of sample was diluted with 1×PBS buffer, and then added into a sample cell of the ParticleMetrix nanosystem for detection.

(5) After the detection was completed, data processing was conducted using software Zeta View 8.04.02 SP2 to record the particle concentration and particle size distribution of sEVs.

Figure 1B:
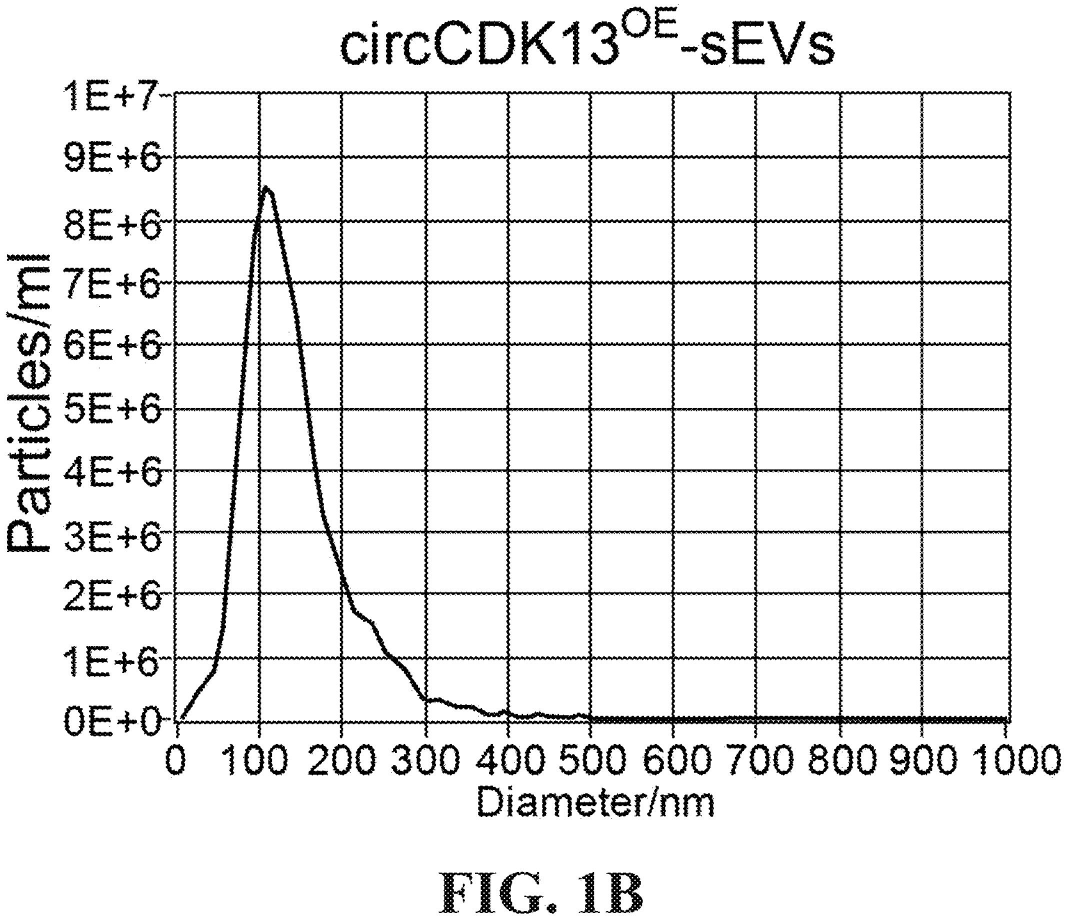
Figure 2A:
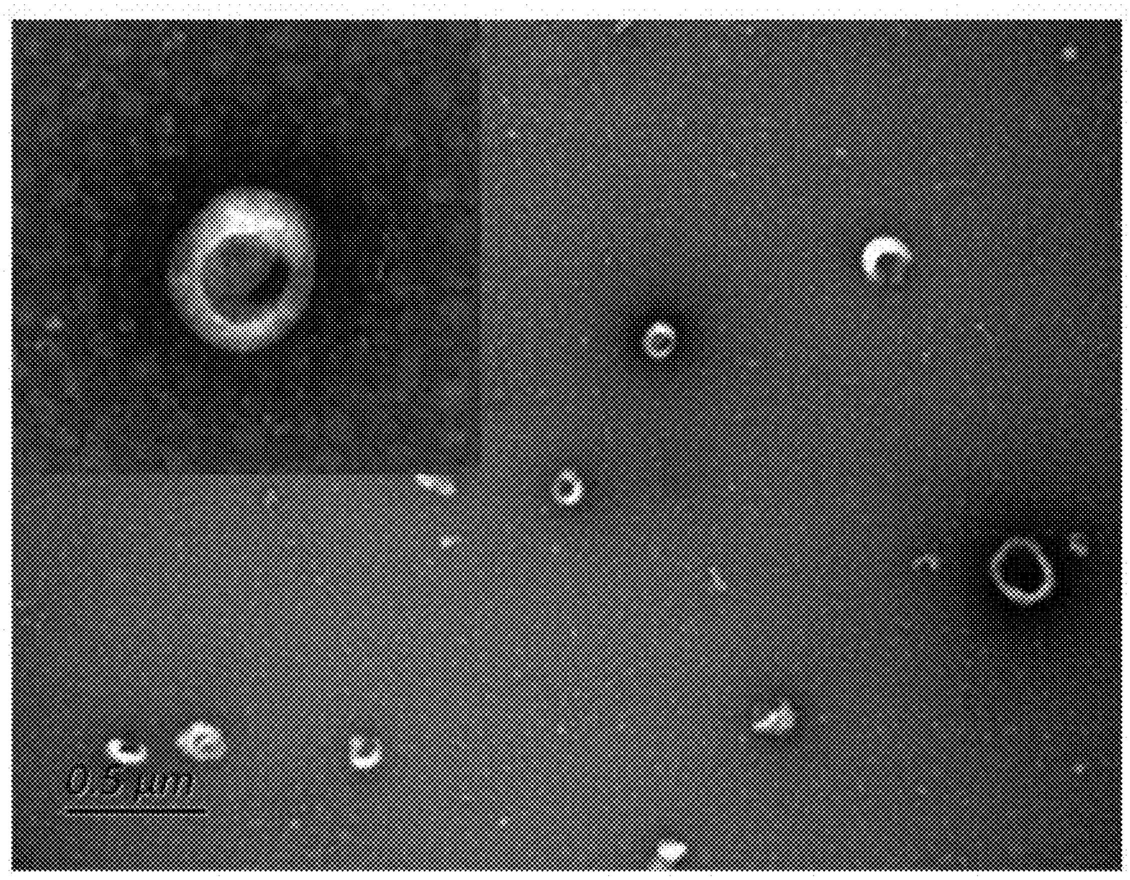
FIGS. 2A-2B show transmission electron microscopy (TEM) image of the hP-MSC E-sEV in Example 1 of the present disclosure.
Figure 2B:
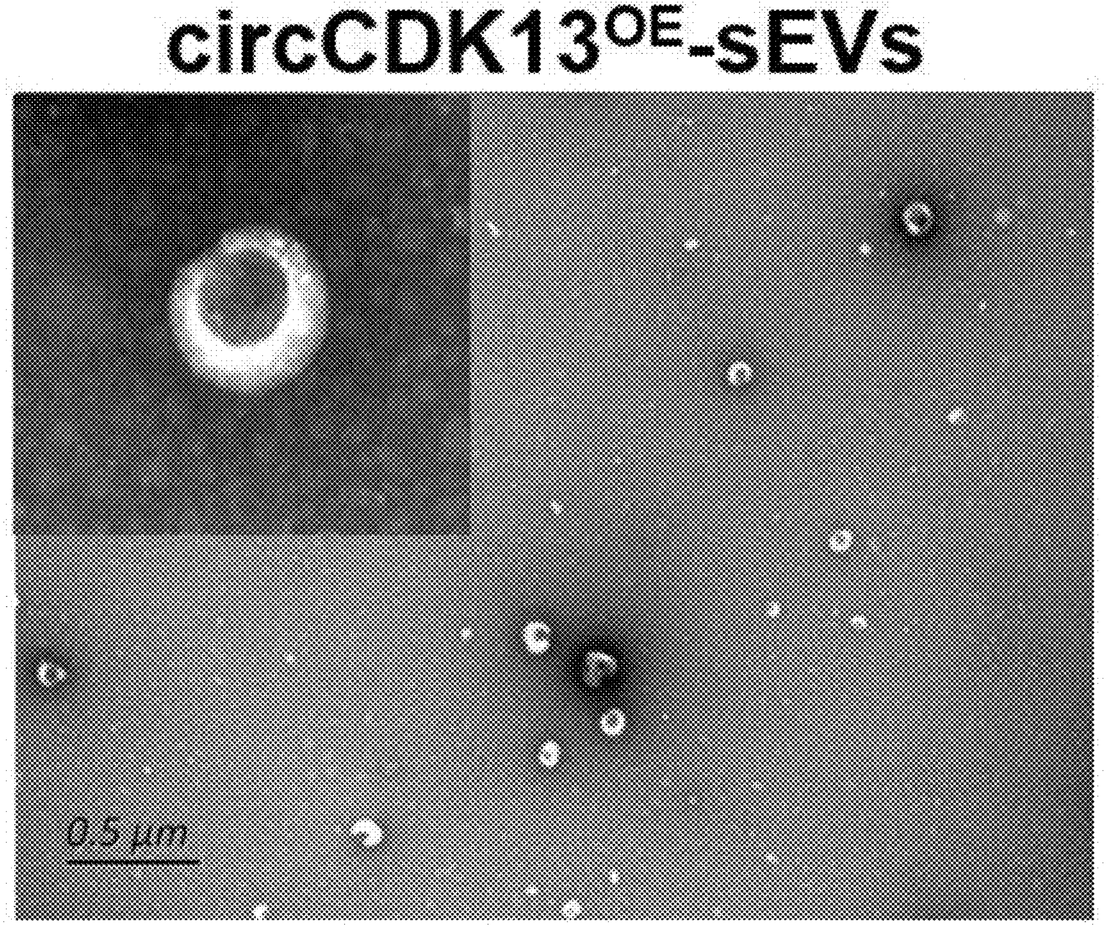
Figure 3:
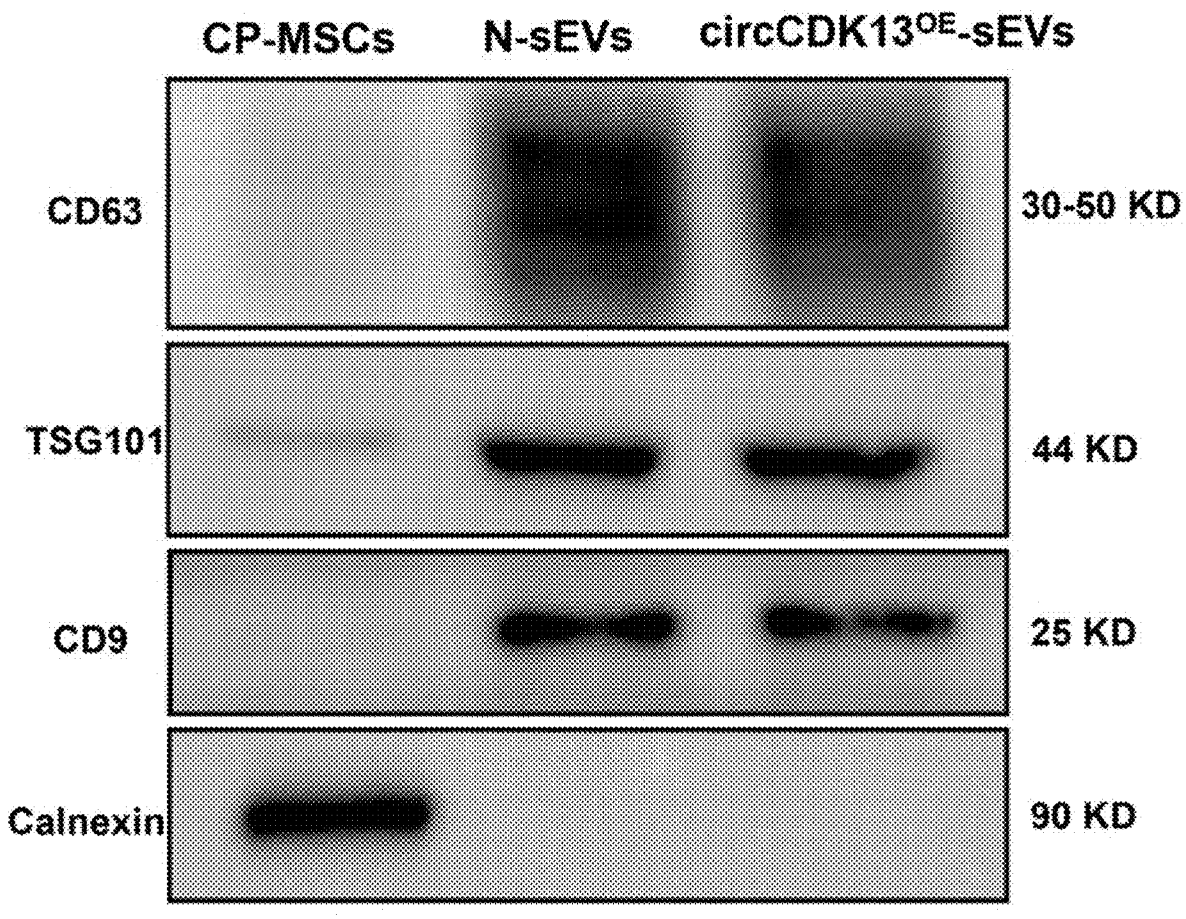
FIG. 3 shows an expression diagram of surface-specific marker proteins of the hP-MSC E-sEV in Example 2 of the present disclosure.

The results were shown in FIGS. 1A-1B to FIG. 3. TEM observed that sEVs had a typical cup-shaped structure (FIGS. 2A-2B), and NTA showed that their average diameter was approximately 114 nm (FIGS. 1A-1B). Overexpression of the circCDK13 did not affect the appearance and diameter of sEVs. In addition, Western blot experiments of the characteristic membrane proteins of sEVs (CD63, CD9, and TSG101) further confirmed the identity of sEVs (FIG. 3)

5. qRT-PCR detection (1) Extraction of total RNA

Total RNAs from cells and sEVs were extracted using a Steady Pure Rapid RNA Extraction Kit.

(2) Reverse transcription of RNA into cDNA

The RNA was reverse transcribed into cDNA using an Evo M-MLV Reverse Transcription Reagent Master Mix Kit.

(3) RT-qPCR a. Primer synthesis: primers were synthesized by Suzhou Synbio Technologies Co., Ltd.

b. Primer dilution: before diluting, the primers were centrifuged at 4,000 rpm for 1 min, then added with an appropriate amount of RNase free water according to the instructions, and the primers shown in Table 1 were diluted to 10 μM.

TABLE 1

Primer sequences of qRT-qPCR

| Gene name | Sequence (5'-3') | SEQ ID NO. |
|---|---|---|
| circCDK13 | F: GCCAAGGAGAAGGAGCAACAT | 1 |
| | R: GAATACGGGCTTCTGCTTCG | 2 |
| GAPDH | F: AGAAGGCTGGGGCTCATTTG | 3 |
| | R: GCAGGAGGCATTGCTGATGAT | 4 |

c. Preparation of reaction solution: the reaction solution was preferably prepared on ice. A preparation method of the reaction solution was shown in Table 2.

TABLE 2 qRT-PCR reaction system

| Reagent name | Consumption (μL) | Final concentration |
|---|---|---|
| 2 × SYBR ® Green Pro Taq HS Premix II | 10 | 1× |
| ROX Reference Dye (4 μM) | 0.4 | 0.08 μM |
| PCR Forward Primer (10 μM) | 0.8 | 0.4 μM*1 |
| PCR Reverse Primer (10 μM) | 0.8 | 0.4 μM*1 |
| Template | | <100 ng*2 |
| RNase Free $dH_2O$ | Up to 20 | |

*1Generally, better results could be obtained with a final primer concentration of 0.4 μM. When the reaction performance was poor, the primer concentration could be adjusted within a range of 0.1 μM to 1.0 μM.

*2In a 20 μL system, the amount of DNA template added was generally less than 100 ng. If necessary, gradient dilution was conducted to determine the appropriate amount of template added. In addition, the volume of cDNA stock solution should not exceed 10% of a total volume of the qPCR reaction.

d. PCR reaction program

Initial denaturation: 95° C. for 30 sec, 1 cycle;

PCR: 95° C. for 5 sec, 60° C. for 30 sec, 40 cycles;

Dissolution curve: 95° C. for 15 sec, 60° C. for 1 min, 95° C. for 15 sec, 1 cycle.

e. The reaction solution was transferred to a PCR amplification microplate, the plate was sealed with Micro Amp™M optical adhesive sealing film, centrifuged at 1,000 rpm for 1 min, and then detected using a Quant Studio5 fluorescence quantitative PCR instrument.

Figure 4A:
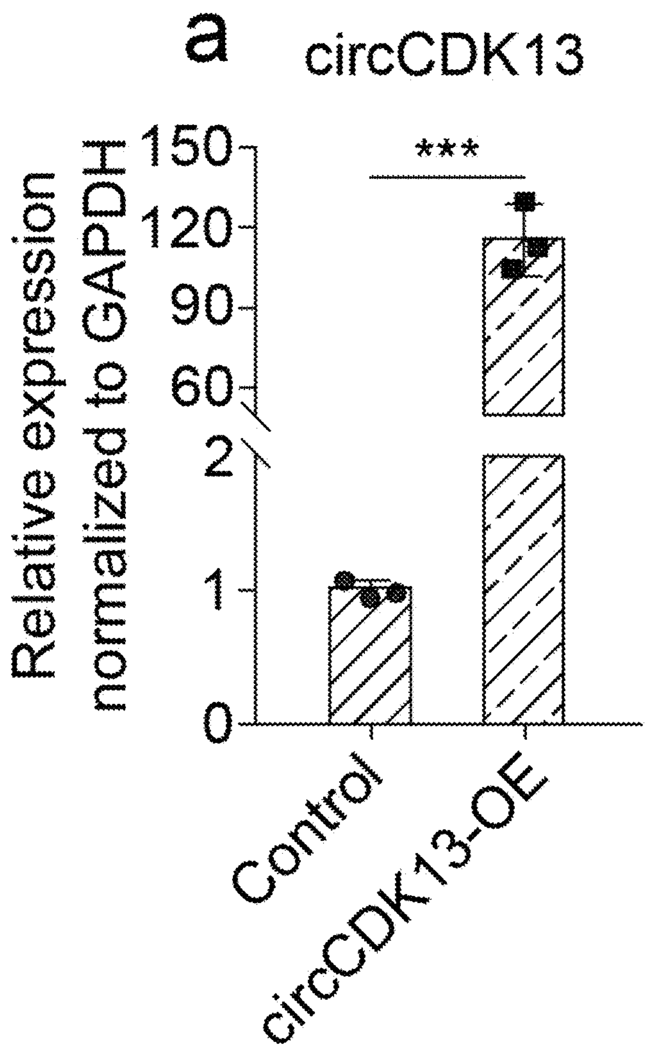
FIGS. 4A-4C show expression level of circCDK13 in the hP-MSC E-sEV in Example 2 of the present disclosure.
Figure 4B:
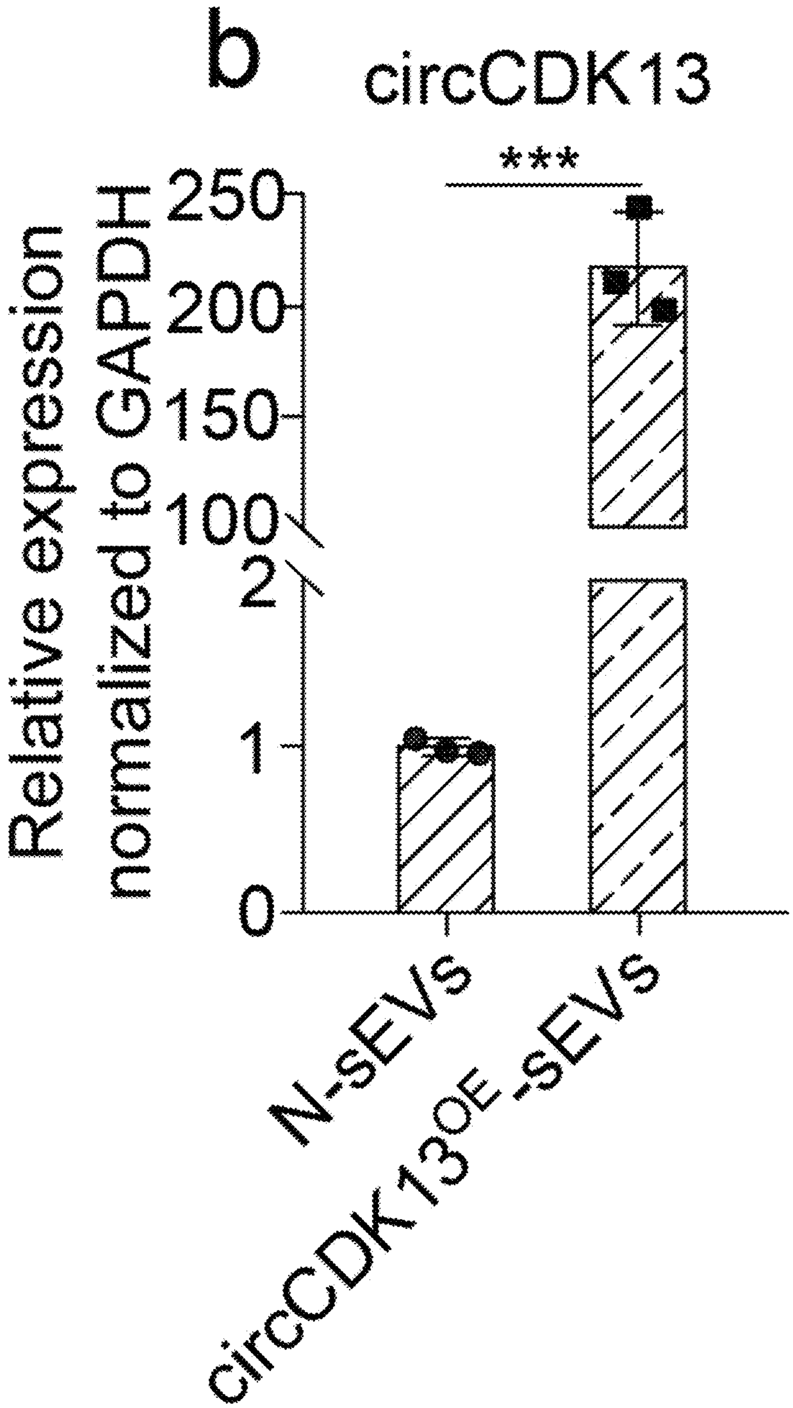
Figure 4C:
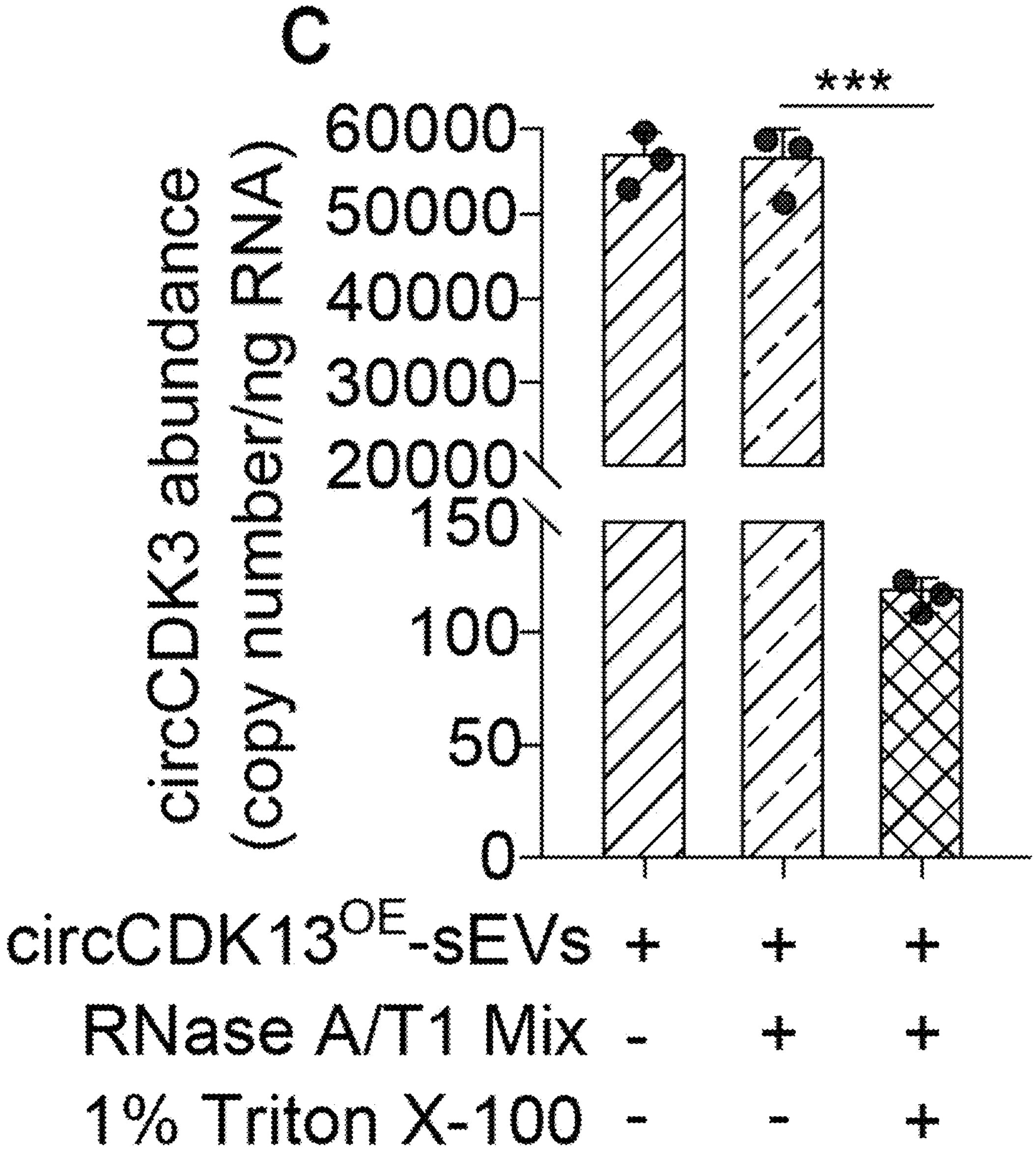

The results were shown in FIGS. 4A-4C. Compared with N-sEVs, the abundance of circCDK13 in circCDK13-sEVs increased significantly, indicating that circCDK13 overexpressed in CP-MSCs was successfully loaded into the sEVs.

6. Protection experiment of CircCDK13 in sEVs circCDK13-sEVs ($1.02\times10^{12}$ particles) and 20 μL of RNase A/T1 mixture were incubated with or without 1% Triton X-100 at 37° C. for 30 min. After incubating at 75° C. for 5 min and inactivating the RNase, a total RNA was extracted using a Steady Pure Rapid RNA Extraction Kit. A copy number of the circCDK13 was estimated by absolute quantitative PCR.

(1) A 220 bp characteristic fragment containing circCDK13 back-splicing sites was cloned and inserted into a pUC57 vector, where the plasmid was designed and constructed by Hitro Biotech Co., Ltd.

(2) RNAs from cells and sEVs were extracted using a Steady Pure Rapid RNA Extraction Kit.

(3) The concentration of sample RNA was measured using a micro-volume UV spectrophotometer.

(4) The RNA was reverse transcribed into cDNA using an Evo M-MLV Reverse Transcription Reagent Master Mix Kit.

(5) The plasmid was diluted 10 times in sequence, and a standard curve was plotted through real-time PCR.

(6) A calculation formula was as follows:

$$\text{Copy number (copy}/\mu\text{L)} = 6.02\times10^{23}\times\text{plasmid concentration (ng}/\mu\text{L)}\times 10^{-9}/[(\text{number of bases of vector}+\text{number of bases of insert})\times 660](\text{g/mol}).$$

The equations for the amplification curve and standard curve were:

Y=aX+b [a value of the initial amplified copy number log 10 as an abscissa (X), and a corresponding cycle number as an ordinate (Y)].

The copy number of circCDK13 was derived based on a cycle threshold (CT) of circCDK13 using plasmid standard linear equations. The results were shown in FIGS. 4A-C. Only treating circCDK13-sEVs with RNase A/T1 mixture did not reduce the abundance of circCDK13. When 1% Triton X-100 (which could break the double-layer membrane structure of sEVs) combined with RNase A/T1 mixture was used to treat circCDK13-sEVs, the abundance of circCDK13 was significantly reduced. This indicated that the circCDK13 was protected in intact sEVs.

TABLE 3

Copy number statistics of circCDK13

| Grouping | CircCDK13 abundance (copies/ng RNA) | | |
|---|---|---|---|
| CircCDK13$^{OE}$-sEVs | 56459.6 | 59768.5 | 52936.7 |
| CircCDK13$^{OE}$-sEVs + RNase A/T1 Mix | 58653.2 | 51298.9 | 57793.1 |
| CircCDK 13$^{OE}$-sEVs + RNase A/T1 Mix + 1% Triton X-100 | 123.342 | 109.215 | 117.54 |

Example 2

Controlled test on the treatment of DM mice with the circCDK13-sEVs preparation prepared in Example 1

1. Establishment of DM wound model (1) Anesthesia: the experimental animals were anesthetized with sodium pentobarbital (where mice: concentration 1%, dose 0.1 mL/20 g; rats: concentration 3%, dose (0.1-0.2) mL/100 g).

(2) Surgery: the hair from the back surgical area of mice and rats were shaved, iodophor was added to disinfect the surgical area, and then a full-thickness skin excision wound with a diameter of 10 mm was established separately on both sides of the back spine. (Note: all mice and rats after the surgery needed to be kept in separate cages to prevent them from biting each other's wounds.)

(3) Grouping: the wounds were randomly divided into three groups, including a PBS group, an N-sEVs group, and a circCDK13-sEVs group, with 24 wounds in each group.

(4) Administration: PBS (100 μL), N-SEVs (100 μL, $2\times10^{11}$ sEVs/mL), circCDK13-SEVs (100 μL, $2\times10^{11}$ sEVs/mL) were separately subcutaneously injected at 4 points at the wound edge (25 μL for each site) using a microsyringe on the postoperative day and on days 3, 7, 10, 14, and 17 after the surgery.

(5) Photographing and recording: the wound healing was observed while taking photos on the postoperative day and on days 3, 7, 10, 14, 17, and 21 after the surgery. The wound area was calculated using Image J software, and then the wound healing curves of mice in each group were plotted. Wound size=At/A0×100%, where A0 represented an initial area of the wound, and At represented a wound area on day t.

(6) Material collection: the above experimental animals were euthanized by giving an overdose of sodium pentobarbital on days 3, 7, 14, and 21 after the surgery, and then the wound and surrounding normal skin were cut off. The wound was divided into two parts, where one part was fixated in 4% paraformaldehyde for histological examination, while the other part was quickly frozen in liquid nitrogen, and then stored at −80° C. for later use.

Figure 5A:
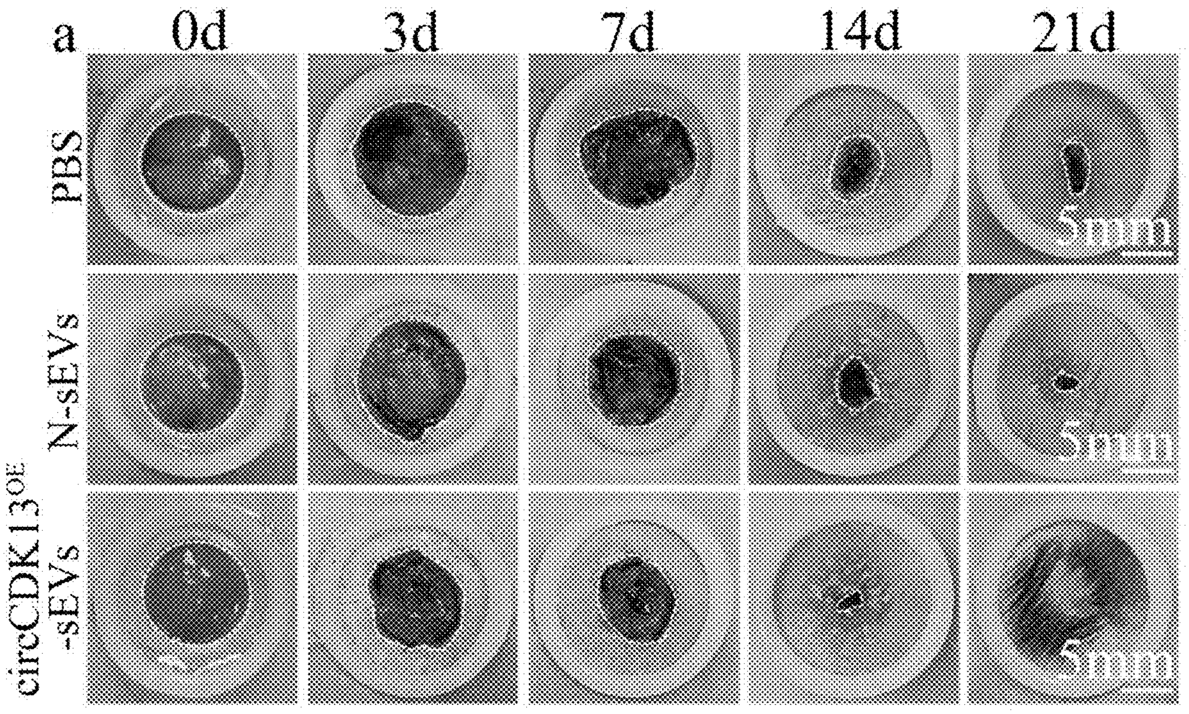
FIGS. 5A-5B show the evaluation and analysis results of an effect in treating a DM mouse wound model using the hP-MSC E-sEV in Example 3 of the present disclosure.
Figure 5B:
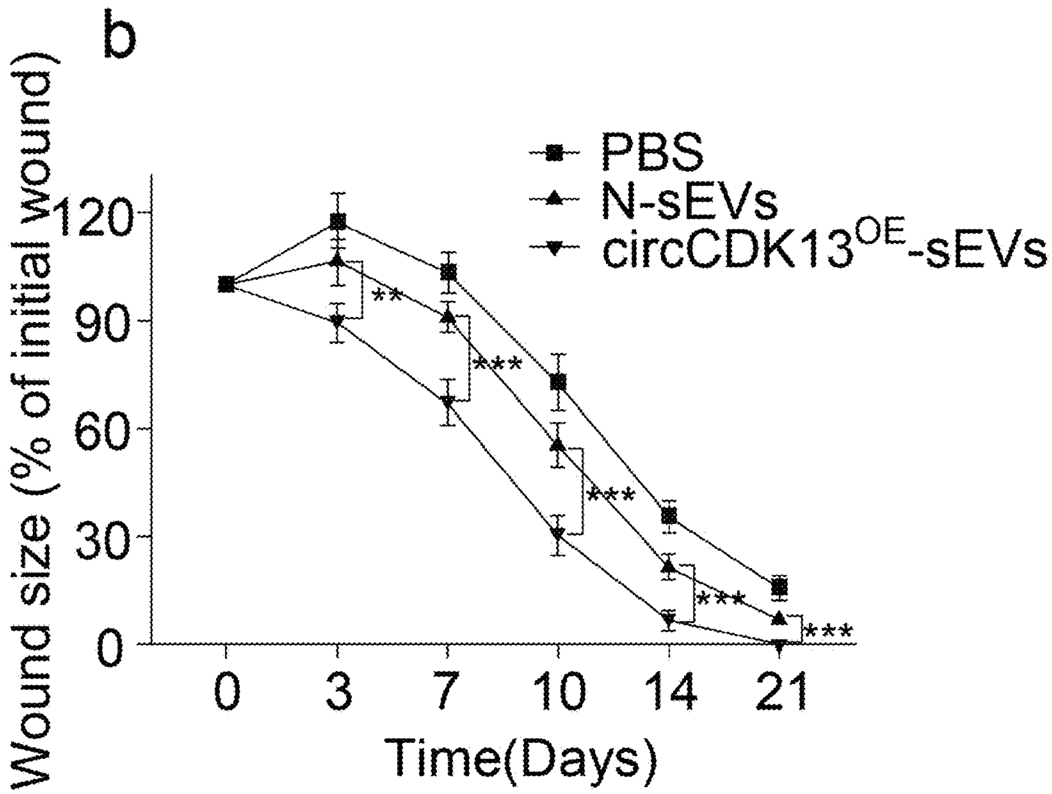

The general view of the wound was shown in FIGS. 5A-5B. On days 7, 14, and 21 after wound surgery, the wounds treated with N-sEVs had smaller wound areas than those in the PBS group. Compared with the N-sEVs group, the wound area treated with circCDK13-sEVs was significantly reduced, and obvious hair regeneration was observed on day 21 (FIG. 5A). In addition, through quantitative analysis of the wound images at each time point, it was found that the wound areas in the PBS group and N-sEVs group became slightly larger on day 3, and the wounds in each group gradually healed over time. The PBS group had the lowest wound healing rate, followed by the N-sEVs group, and the circCDK13-sEVs group had the highest wound healing rate (FIG. 5B). The above experimental results showed that N-sEVs secreted from CP-MSCs could promote wound healing in DM mice, and the ability of circCDK13-loaded sEVs in promoting the wound healing was significantly enhanced.

2. H&E staining of skin wounds (1) Dehydration: skin samples were dehydrated using a fully automatic dehydration machine.

(2) Embedding: the skin samples were embedded in pathological grade paraffin with a melting point of 56° C. to 58° C.

(3) Slicing: slicing was conducted from the largest transverse diameter of the wound.

(4) Baking slices: the paraffin sections were placed in a constant-temperature drying oven at 60° C. to allow baking before staining.

(5) Dewaxing and hydration of paraffin sections included: dewaxing with xylene (I) for 10 min, dewaxing with xylene (II) for 10 min, absolute ethanol (I) for 2 min, absolute ethanol (II) for 2 min, 95% ethanol for 2 min, 85% ethanol for 2 min, 75% ethanol for 2 min, and distilled water for 2 min.

(6) The sections were stained with hematoxylin dye for 3 min to 10 min and rinsed with tap water for 5 sec to 10 sec.

(7) The sections were differentiated with a differentiation solution (1% hydrochloric acid alcohol) for 1 sec to 5 sec, and rinsed with tap water for 20 sec to 30 sec.

(8) The sections were returned to blue with ammonia (1% ammonia) for 10 sec to 30 sec, and rinsed with tap water for 20 sec to 30 sec.

(9) The sections were stained with eosin for 30 sec to 2 min and rinsed with tap water for 1 sec to 5 sec.

(10) Dehydration and transparency treatment included: 75% ethanol for 2 sec to 3 sec, 85% ethanol for 2 sec to 3 sec, 95% ethanol for 2 sec to 3 sec, absolute ethanol (I) for 2 sec to 3 sec, absolute ethanol (II) for 1 min, xylene (I) for 1 min, and xylene (II) for 1 min.

(11) Sealing and observation: the sections were sealed with neutral gum, and the H&E-stained sections were subjected to panoramic scanning by a fully automatic digital pathology scanner.

Figure 6A:
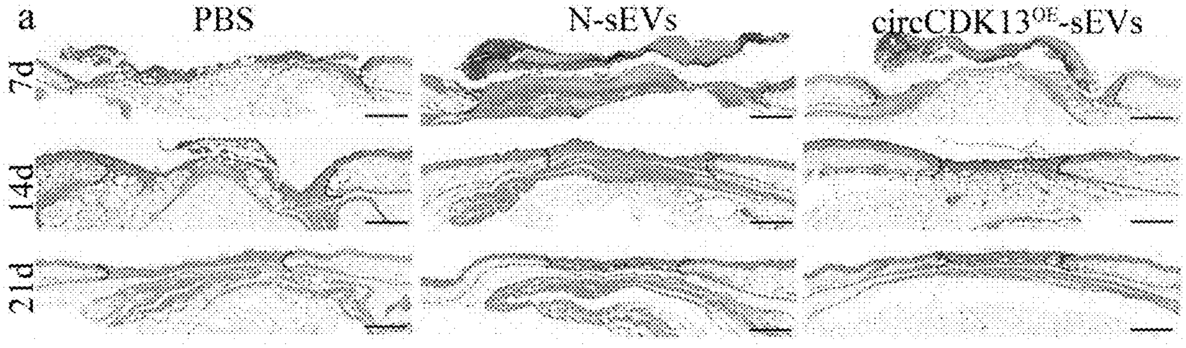
FIGS. 6A-6D show H&E staining of skin wounds on a DM mouse.
Figure 6B:
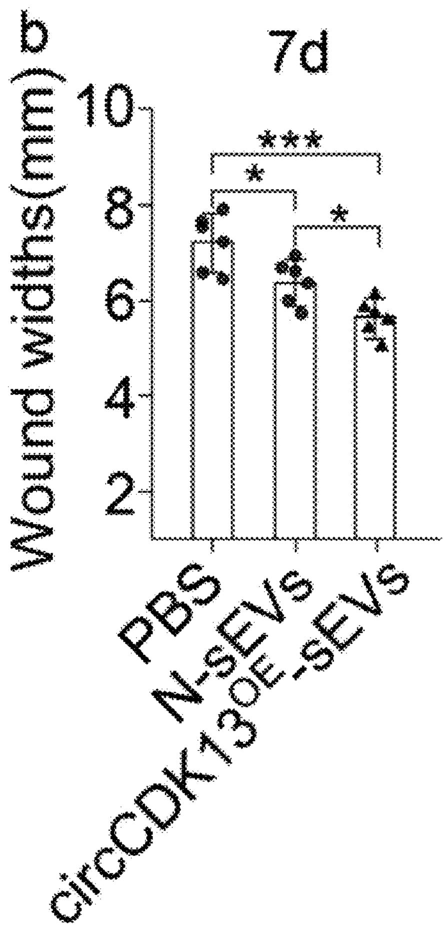
Figure 6C:
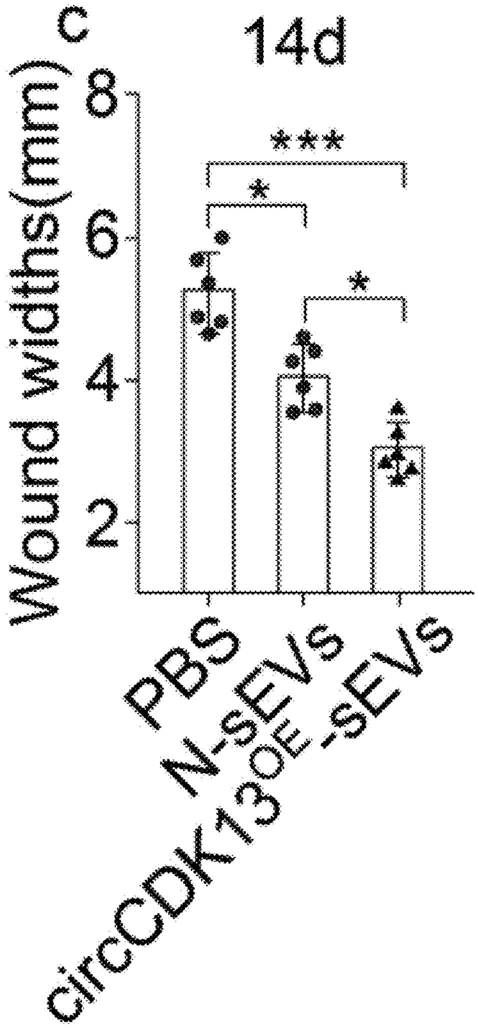
Figure 6D:
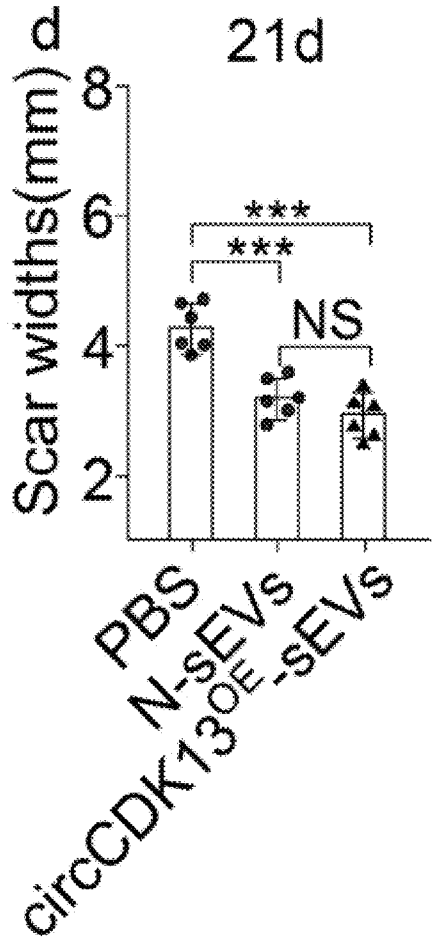

The results were shown in FIGS. 6A-6D. Compared with the N-sEVs group, the circCDK13-sEVs group had a longer and thicker epithelial tongue, indicating that circCDK13-sEVs had a stronger ability to promote epidermal cell proliferation and migration (FIG. 6A). On days 3, 7, 14, and 21 after wound surgery, H&E staining of skin wounds was conducted and quantified. The results showed that the PBS group had the lowest wound healing rate, followed by the N-sEVs group, and the circCDK13-sEVs group had the highest wound healing rate (FIG. 6A). On day 21, no new hair follicles were observed in the wounds of the PBS group, while a large number of regeneration of skin appendages (hair follicles and sebaceous glands) were observed in the wounds of the circCDK13-sEVs group. The above experimental results proved that the circCDK13-sEVs could accelerate wound healing and the regeneration of appendages, making wound repair more perfect.

Although the above example has described the present disclosure in detail, it is only a part of, not all of, the examples of the present disclosure. Other examples may also be obtained by persons based on the example without creative efforts, and all of these examples shall fall within the protection scope of the present disclosure.

What is claimed is:

1. A method for promoting wound healing in diabetes mellitus (DM), the method comprising administering a medicament comprising circCDK13-enriched engineered small extracellular vesicles (E-sEV) to a patient in need thereof.

2. The method according to claim 1, wherein the circCDK13-enriched E-sEV is prepared by a process comprising the following steps:

infecting a mesenchymal stem cell (MSC) with a vector expressing circCDK13, and extracting a small extracellular vesicle (sEV) from a resulting infected positive MSC to obtain the circCDK13-enriched E-sEV.

3. The method according to claim 2, wherein the vector expressing the circCDK13 comprises a lentivirus-overexpressing expressing the circCDK13.

4. The method according to claim 2, after obtaining the infected positive MSC, further comprising culturing the infected positive MSC, collecting a resulting cell supernatant, and extracting the circCDK13-enriched E-sEV from the cell supernatant.

5. The method according to claim 4, wherein the infected positive MSC is cultured in an MSC-specific serum-free medium.

6. The method according to claim 2, wherein a process of the extracting comprises differential centrifugation.

7. The method according to claim 4, wherein a process of the extracting comprises differential centrifugation.

8. The method according to claim 6, wherein the differential centrifugation comprises: subjecting the infected positive MSC to first centrifugation, subjecting an obtained first centrifugation supernatant to second centrifugation, subjecting an obtained second centrifugation supernatant to third centrifugation, and collecting an obtained precipitate; the first centrifugation is conducted at 3,000 g to 4,000 g, the second centrifugation is conducted at 10,000 g to 12,000 g, and the third centrifugation is conducted at 100,000 g to 200,000 g.

9. The method according to claim 7, wherein the differential centrifugation comprises: subjecting the infected positive MSC to first centrifugation, subjecting an obtained first centrifugation supernatant to second centrifugation, subjecting an obtained second centrifugation supernatant to third centrifugation, and collecting an obtained precipitate; the first centrifugation is conducted at 3,000 g to 4,000 g, the second centrifugation is conducted at 10,000 g to 12,000 g, and the third centrifugation is conducted at 100,000 g to 200,000 g.

10. The method according to claim 8, wherein the first centrifugation is conducted for 15 min; the second centrifugation is conducted for 60 min; and the third centrifugation is conducted for 90 min.

11. The method according to claim 9, wherein the first centrifugation is conducted for 15 min; the second centrifugation is conducted for 60 min; and the third centrifugation is conducted for 90 min.

12. The method according to claim 8, wherein the second centrifugation supernatant is filtered with a filter membrane having a pore size of 0.22 μm before the third centrifugation is conducted.

13. The method according to claim 9, wherein the second centrifugation supernatant is filtered with a filter membrane having a pore size of 0.22 μm before the third centrifugation is conducted.

* * * * *

```
                              SEQUENCE LISTING


Sequence total quantity: 4
SEQ ID NO: 1              moltype = DNA  length = 21
FEATURE                   Location/Qualifiers
source                    1..21
                          mol_type = other DNA
                          note = Sequence of forward primer for qRT-qPCR of circCDK13
                          organism = synthetic construct
SEQUENCE: 1
gccaaggaga aggagcaaca t                                               21

SEQ ID NO: 2              moltype = DNA  length = 20
FEATURE                   Location/Qualifiers
source                    1..20
                          mol_type = other DNA
                          note = Sequence of reverse primer for qRT-qPCR of circCDK13
                          organism = synthetic construct
SEQUENCE: 2
gaatacgggc ttctgcttcg                                                 20

SEQ ID NO: 3              moltype = DNA  length = 20
FEATURE                   Location/Qualifiers
source                    1..20
                          mol_type = other DNA
                          note = Sequence of forward primer for qRT-qPCR of GAPDH
                          organism = synthetic construct
SEQUENCE: 3
agaaggctgg ggctcatttg                                                 20

SEQ ID NO: 4              moltype = DNA  length = 21
FEATURE                   Location/Qualifiers
source                    1..21
                          mol_type = other DNA
                          note = Sequence of reverse primer for qRT-qPCR of GAPDH
                          organism = synthetic construct
SEQUENCE: 4
gcaggaggca ttgctgatga t                                               21
```